United States Patent [19]
Weichselbaum

[11] Patent Number: 4,790,308
[45] Date of Patent: Dec. 13, 1988

[54] NASAL CANNULA HARNESS

[75] Inventor: Edwin G. Weichselbaum, Eureka, Mo.

[73] Assignee: Sherwood Medical Company, St. Louis, Mo.

[21] Appl. No.: 596,754

[22] Filed: Apr. 4, 1984

[51] Int. Cl.⁴ .............................................. A61M 15/08
[52] U.S. Cl. .................................................. 128/207.18
[58] Field of Search ...................... 128/206.11, 203.22, 128/207.18, D26, 207.14, 207.15, 207.17; 604/94, 162; 138/117

[56] References Cited

U.S. PATENT DOCUMENTS

| Re. 29,487 | 12/1977 | Gardner, Jr. | 128/152 |
|---|---|---|---|
| 718,785 | 1/1903 | McNary | |
| 853,439 | 5/1907 | Clark | 128/207.18 |
| 2,647,072 | 7/1953 | Smith | 154/90 |
| 2,663,297 | 12/1953 | Turnberg | 128/206 |
| 2,735,432 | 2/1956 | Hudson | 128/348 |
| 2,931,358 | 4/1960 | Sheridan | 128/206 |
| 3,400,714 | 9/1968 | Sheridan | 128/206 |
| 3,574,306 | 4/1971 | Alden | 604/162 |
| 3,643,660 | 2/1972 | Hudson et al. | 128/206 |
| 3,726,275 | 4/1973 | Jackson et al. | 128/206 |
| 3,802,431 | 4/1974 | Farr | 128/206 |
| 3,834,380 | 9/1974 | Boyd | 128/133 |
| 3,915,173 | 10/1975 | Brekke | 128/351 |
| 3,993,081 | 11/1976 | Cussell | 128/207.18 |
| 4,106,505 | 8/1978 | Salter et al. | 128/206 |
| 4,122,857 | 10/1978 | Haerr | 128/DIG. 26 |
| 4,156,426 | 5/1979 | Gold | 128/205 |
| 4,278,082 | 7/1981 | Blackmer | 128/207.18 |
| 4,336,806 | 6/1982 | Eldridge | 128/348 |
| 4,363,323 | 12/1982 | Geiss | 128/207.18 |
| 4,367,735 | 1/1983 | Dali | 128/207.18 |
| 4,648,398 | 3/1987 | Agdanowski et al. | 128/207.18 |

FOREIGN PATENT DOCUMENTS 604065 8/1960 Canada .

Primary Examiner—Lee S. Cohen
Assistant Examiner—David Shay
Attorney, Agent, or Firm—Stanley N. Garber; Andrew J. Beck; William R. O'Meara

[57] ABSTRACT

A nasal cannula harness is provided which includes a pair of sheet members in facing relation and holding the distal end portions of a pair of narine tubes in position for insertion into the nares of a patient. The nasal cannula harness may be made by folding a molded sheet member and securing the sections of the folded member together with the distal portions of the narine tubes between the sections and with portions extending outwardly for insertion into the nares of a patient.

17 Claims, 3 Drawing Sheets

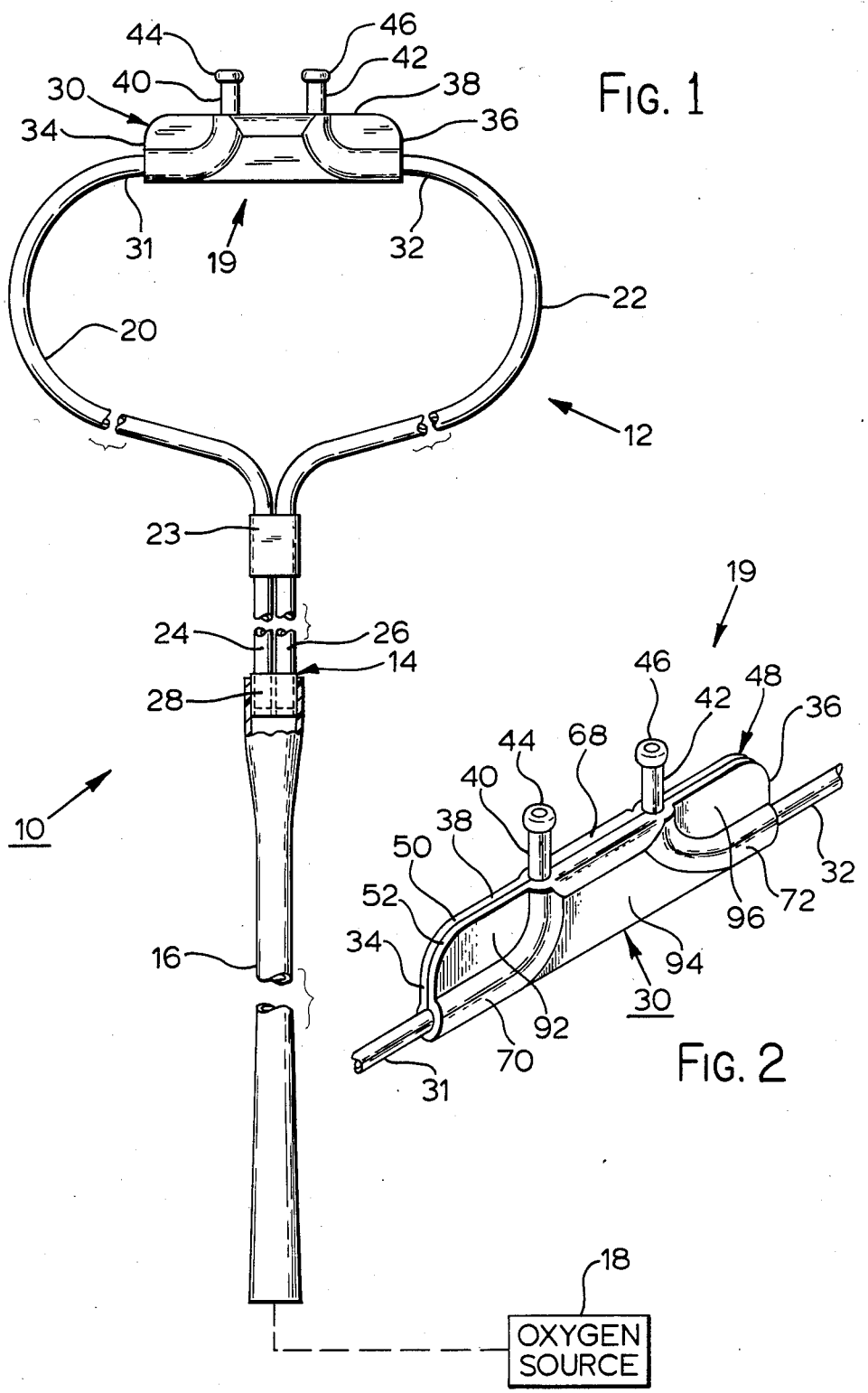

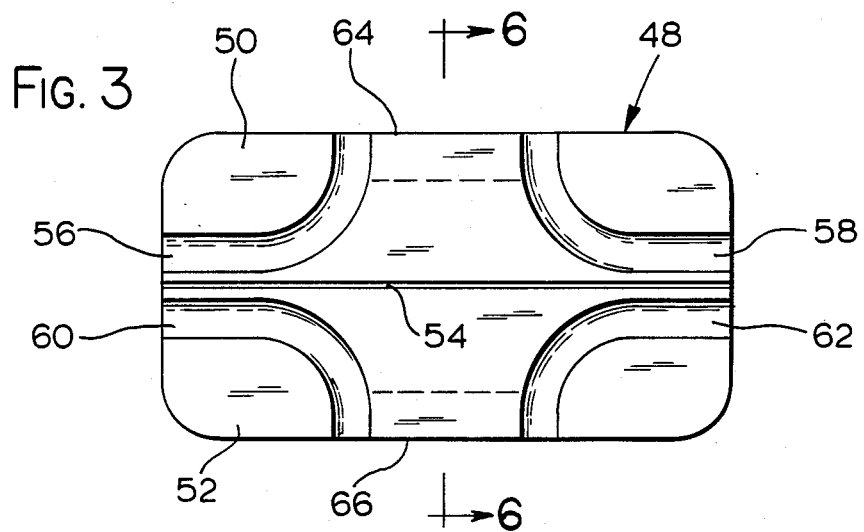
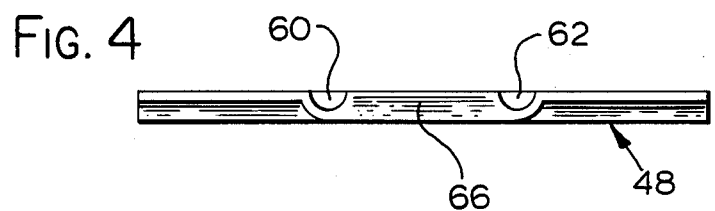
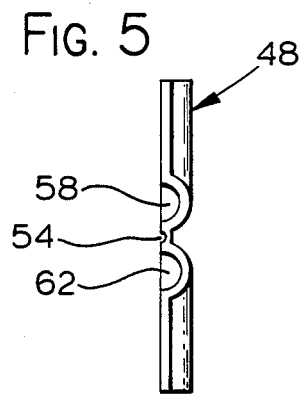
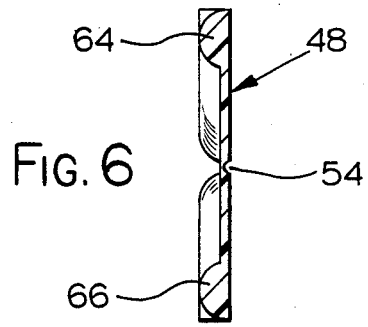

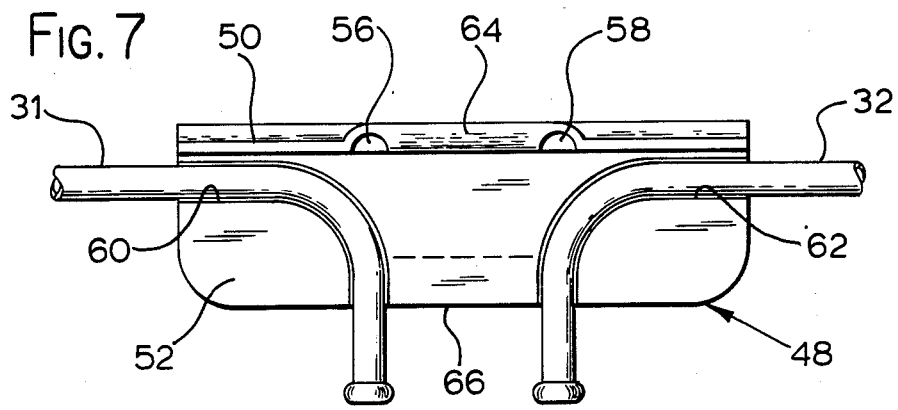
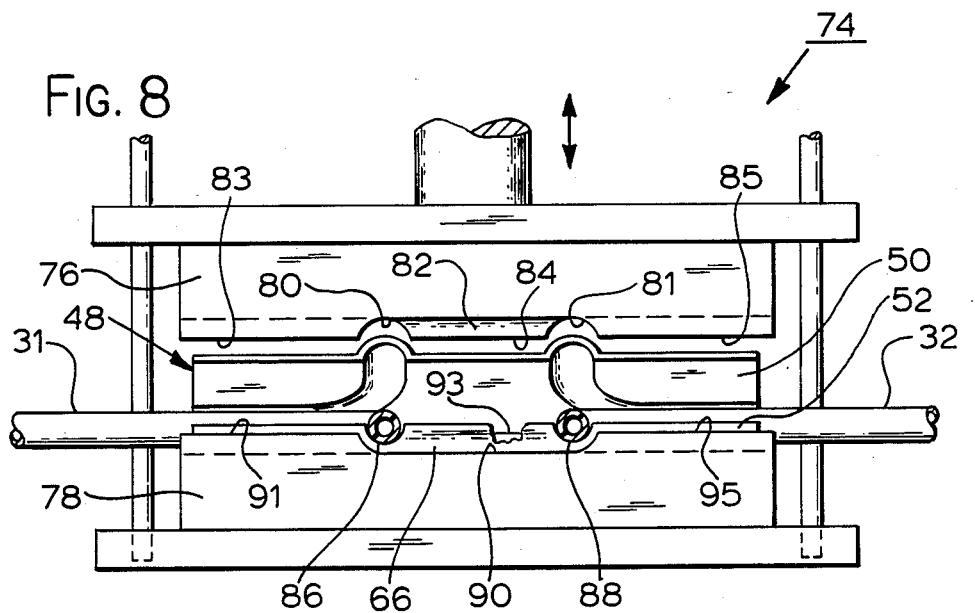
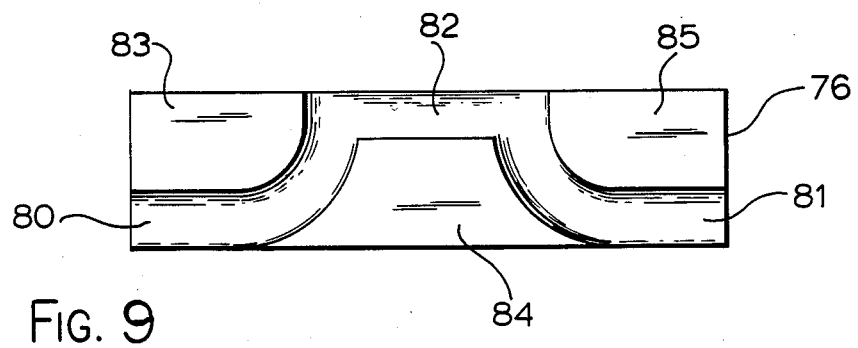

NASAL CANNULA HARNESS

TECHNICAL FIELD

This invention relates to nasal cannula harnesses for supplying gas to the nasal passages of a patient and to the method of making the same.

BACKGROUND ART

Nasal cannula harnesses which are employed to administer gases, such as oxygen, to the nasal passages of a patient, often require a relatively expensive nasal cannula. For example, a nasal cannual may include a hollow molded bridge member having integrally molded narine tubes and with the bridge member connected to a pair of gas supply tubes. Such hollow bridge members are relatively expensive to mold. In some cases, narine tubes are inserted through holes in a tubular bridge member. With the latter type of bridge, the narine tubes are generally not securely held against relative movement and bending so that there is a possibility that administration gas may be interrupted if a tube becomes bent in use. Also, such a tubular bridge member may become so flexible that the narine tubes are difficult to manage or be inserted and maintained within the nares of the patient.

DISCLOSURE OF THE INVENTION

It is therefore an object of the present invention to provide an improved nasal cannula harness having a nasal cannula which is economical in construction and to manufacture, and which overcomes one or more of the above mentioned problems or disadvantages of prior art devices.

Another object is to provide a nasal cannula having an improved bridge for the narine tubes and to an improved method of making the same, and which is simple and economical in construction, and which provides good support for the narine tubes.

In accordance with one aspect of the present invention, a nasal cannula harness is provided which includes a pair of sheet members secured together in facing relation with a pair of narine tubes extending between the sheet members and from one side thereof, the tubes being adapted for insertion into the nares of a patient. In accordance with another aspect of the present invention, a pair of narine tubes are positioned between a pair of sheet members and the sheets members are clamped and secured together in areas on each side of the tubes. In accordance with still another aspect of the present invention, a first section of a sheet member is provided with channels for receiving and locating a pair of narine tubes, and a second section of the sheet member is folded over the tubes and secured in facing relation with the first section to secure the narine tubes between the sections.

These, as well as other objects and advantages of the invention, will become apparent from the following detail description and accompanying drawings.

BRIEF DESCRIPTION OF THE DRAWINGS

FIG. 1 is a plan view of a nasal cannula harness assembly in accordance with a preferred embodiment of the present invention;

FIG. 2 is a prospective view on an enlarged scale of the nasal cannula of FIG. 1;

FIG. 3 is a plan view on an enlarged scale of a molded sheet member used in making the nasal cannula of FIG. 1;

FIG. 4 is a bottom side view of the sheet member of FIG. 3;

FIG. 5 is a right end view of the sheet member of FIG. 3;

FIG. 6 is a cross-sectional view taken along the line 6—6 of FIG. 3;

FIG. 7 illustrates a step in the manufacture of the nasal cannula of FIG. 1;

FIG. 8 shows a clamping die assembly which may be used in the manufacture of the nasal cannula of FIG. 1; and FIG. 9 is a bottom plan view of the upper die member of the clamping die of FIG. 9.

DETAILED DESCRIPTION OF THE PREFERRED EMBODIMENT

Referring now to the drawings, and particularly to FIG. 1, a nasal cannual harness assembly 10 is shown including a nasal cannual harness 12 connected through a tube connector 14 to a main gas supply tube 16 which, in turn, is adapted for connection to a source of gas 18, for example, a source of oxygen or other suitable therapeutic gas.

The nasal cannula harness 12 is shown including a nasal cannula 19, a pair of narine gas supply tubes 20 and 22, and a slip ring 23. The narine tubes have proximal end portions 24 and 26, respectively, connected in sealing relation in a pair of openings extending through a resilient connector plug member 28 of connector 14. Plug 28 may be of rubber or plastic and is shown in fluid tight connection within the distal end of gas supply tube 16. Tube 16 has a greater inner diameter than either of the narine tubes 20 and 22 so as to provide sufficient flow of gas to the nasal cannula harness 12. The nasal cannula 19 includes a bridge 30 connecting distal end portions 31 and 32 of the narine tubes 20 and 22, respectively, in predetermined relationship.

As also is seen in FIG. 2, the distal end portions 31 and 32 of the narine tubes 20 and 22 extend into the opposed ends 34 and 36, respectively, of the bridge 30 and smoothly curve upwardly to and beyond the upper side 38 of the bridge. As shown, the end portions 31 and 32 have external end portions or extensions indicated at 40 and 42, respectively, that are adapted to be received in the nares of a patient. The nare receiving extensions 40 and 42 extend approximately parallel to each other and are shown provided with smoothly rounded, radially outwardly extending rings or flanges 44 and 46, respectively, at the distal ends thereof and provide a desirable fit within the nares of patient when the nasal harness 12 is in use.

The bridge 30 is preferably formed from a unitary or singel-piece molded sheet member 48 which is folded back upon itself to provide a pair of facing sheet members or sections 50 and 52. The distal end portions 31 and 32 of the narine tubes are clamped between the sheet sections 50 and 52 with the sheet sections secured to one another in areas on opposed sides of each of the tube end portions 31 and 32. The sheet member 48 may be made of rubber or other plastic and is preferably formed of a flexible plastic such as polyvinyl chloride, polyethylene, or other suitable thermoplastic material.

The sheet member 48 is shown prior to its assembly within the narine tubes in FIGS. 3–7. Member 48 has a longitudinally extending fold groove 54 providing a hinge extending from the left end to the right end of the sheet member, as viewed in FIG. 7, which divides the member into sheet sections 50 and 52. The groove 54 facilitates folding of the sheet member 48 about the narine tubes. As best seen in FIG. 3, sheet section 50 has a pair of grooves or channels 56 and 58 formed in its inner side which extend inwardly from the left and right ends, respectively, of the section and then smoothly curve upwardly to the upper edge of the section, Section 52 also has a pair of grooves or channels indicated at 60 and 62 which extend inwardly from the left and right ends of the section, respectively, and smoothly curve downwardly to the lower edge of the section. The left ends of channels 56 and 60 and the right ends of the channels 58 and 62 are adjacent the fold groove 54.

The sheet member 48 is shown having a substantially constant thickness throughout except at the fold groove 54 and in areas between the channels and adjacent the upper and lower edges of the sheet member. As seen best in FIGS. 3, 4, 6 and 7, the sheet member is provided with a rounded thickened portion 64 extending longitudinally adjacent the upper edge of the sheet member between the channels 56 and 58. Also, a similar rounded thickened portion 66 is shown extending longitudinally adjacent the lower edge of the sheet member between channels 60 and 62. The rounded portions 64 and 66 in the finished bridge shown in FIG. 2, provide a smoothly rounded nose rest 68 which generally engages the nose of the patient when the harness 12 is in use.

In assembling the bridge 30 with the narine tubes 20 and 22, the distal end portions 31 and 32 may be inserted, for example, into the channels 60 and 62 of sheet member section 52 as shown in FIG. 7. The sheet member 48 is shown partially folded about groove 54 with the upper section 50 at 90° to the section 52. The sheet section 50 may be further folded along fold groove 54 and over the tube sections 31 and 32 with the engaging surfaces or a substantial area thereof secured to the complementary surfaces of the sheet section 52 to form the assembly as shown in FIGS. 1 and 2. Surfaces of the sheet sections may be secured together (depending upon the material used) by heat welding, solvent bonding, cementing or in other suitable ways. The channels 56 and 60 are complementary and form a tunnel 70 in the bridge (FIG. 2) through which the distal end portion 31 of tube 20 extends, and the complementary channels 58 and 62 form a tunnel 72 through the bridge 30 and through which the distal end portion 32 of narine tube 22 extends.

In a preferred method of assembling the sheet member 48 to the narine tubes 20 and 22 to form the completed harness 12, a heat welding die assembly 74 of FIG. 8 may be used. The die assembly 74 include upper and lower die members 76 and 78 adapted to be heated and which have facing surfaces that are mirror images of each other. The upper die member 76, as shown in FIG. 9, includes a pair of channels 80 and 81 generally complementary to and which receive the channels 56 and 58 of the sheet section 50 during assembly. The die channels 80 and 81 are connected by a longitudinally extending channel or recess indicated at 82 which is complementary to and is adapted to receive the rounded longitudinally extending portion 64 of sheet section 50. The bottom face of die member 76 also has flat heat sealing or welding portions 83, 84 and 85 adapted to engage the flat portions of sheet section 50 during welding. The lower die member 78 includes die channels 86 and 88 for receiving channels 60 and 62 of section 52 and it has a longitudinally extending recess 90 which accommodates rounded portion 66 of the sheet section 52. Die member 78 also has flat heat welding areas 91, 93 and 95 which engage flat portions of sheet section 52 and are complementary to and cooperate with areas 83, 84 and 85 of die member 76 to weld the sections 50 and 52 together.

In using the heat welding die assembly 74, the distal end portions 31 and 32 of the narine tubes may be inserted into the channels 60 and 62 of sheet section 52 as indicated in FIG. 7. The sheet section 50 may be further folded along the fold groove 54 until it forms an acute angle with the sheet section 52. This may be done in the die assembly in some cases, or a partially folded sheet member 48 may be inserted into the lower die member 78 with the channels 70 and 62 of section 52 inserted into channels 86 and 88 of the lower die member 78 as shown in FIG. 8. When the die members 76 and 78 are closed or member 76 is moved downwardly to clamp the sheet sections 50 and 52 together, the channels in the upper and lower die members receive the complementary channels of the sheet member 48, and the rounded portions 64 and 66 are respectively received in channels 82 and 90 of the die members. In this way, the welding portions 83, 84 and 85 of the upper die 76 cooperate respectively with welding portions 91, 93 and 95 of lower die member 78 to engage and heat seal or weld the facing flat areas of the sheet sections together to form the flat portions 92, 94 and 96 (FIG. 2) of the finished bridge 30. These flat welded portions 92, 94 and 96 of the bridge 30 maintain the tubes securely located in the tunnels 70 and 72. Preferably, the tunnels 70 and 72 are sized relative to the size of the narine tubes such that the inner sidewalls of the tunnels frictionally engage the outer surfaces of the tube portions 31 and 32 to maintan them in fixed relationship with the bridge 30. In this way, it is generally not necessary to effect a heat or other bond between the outer surface of the narine tubes 20 and 22 and the inner surfaces of the tunnels 70 and 72 in order to prevent relative movement between the tubes and bridge.

Die assembly 74 may be used, instead of using heat welding, to solvent bond or cement the flat facing surfaces together. Where welding is employed, well known ultrahigh frequency or radio frequency welding may be employed to assemble the bridge and tubes. The inner flat facing sides of the portions 64 and 66 that form the nose rest 68 may also be fixed together.

In use, the two narine tube extensions 40 and 42 are inserted into the nares of the patient with the tubes 20 and 22 generally extending over and behind the ears and downwardly to a point below the chin. The slip ring 23 may be adjusted to provide a desirable harness fit.

The sheet sections of the bridge 30 may be easily and economically molded from flat plastic sheet stock. The bridges are especially economically and simple to make when the bridge sections are of a single unitary molded part such as shown for illustration in the drawings. Also, the assembling of the narine tubes 20 and 22 with the sheet member 48 is simple and economical to perform. The narine tubes in the finished harness are firmly held in the desired location by the tunnels 70 and 72. The sheet member channels forming the tunnels facilitate the manufacture of the nasal cannula harness since the narine tubes may be easily manually bent or curved to fit within the channels. The channels readily predeterminately shape and maintain the distal end portions of the narine tubes in a desired configuration during assembly.

The narine tubes 20 and 22, the slip ring 23, and supply tube 16 may be made of any suitable rubber or plastic. For example, they may be extruded from polyvinyl chloride or polyethylene.

As various changes could be made in the above construction and method without departing from the scope of the invention, it is intended that all matter contained in the above description and shown in the accompanying drawings be interpreted as illustrative and not in a limiting sense.

What is claimed is:

1. A nasal cannula harness for delivering gas to the nasal passages of a patient comprising a pair of flexible tubes each having opposed end portions, one end portion of each of said tubes being adapted for connection to gas supply means, and a bridge connected to the other end portion of each of said tubes and holding the same for insertion into the nares of the patient, said bridge including a pair of sheet members, said other end portions of said tubes extending between said sheet member, said sheet members having inner sides with portions secured together in facing relation at locations on opposed sides of each of said other end portions of said tubes, said bridge having opposed bottom and upper sides and opposed longitudinally spaced ends, said other end portions of said tubes extending longitudinally into said opposed ends of said bridge, respectively, and upwardly and out of said upper side of said bridge for insertion into the nares of the patient.

2. The harness of claim 1 wherein said bridge includes a first channel in the inner wall of one of said sheet members extending inwardly and curving upwardly toward said upper side and receiving and locating one of said end portions, and a second channel in the inner wall of one of said sheet members extending inwardly and curving upwardly toward said upper side and receiving and locating the other of said end portions.

3. The harness of claim 2 wherein said channels extend respectively from said opposed ends of said bridge to said upper side of said bridge.

4. The harness of claim 1 wherein said sheet members comprise a folded single-piece of material having a fold along one of said sides of said bridge.

5. The harness of claim 4 wherein said secured together sheet member portions include flat areas of said sheet members adjacent each side of said tube end portions.

6. The harness of claim 3 wherein said sheet members comprise a folded single-piece of material having a fold along said bottom side of said bridge.

7. The harness of claim 1 wherein each of said other end portions of said tubes is curved and has a substantially straight portion extending outwardly from said upper side of said bridge for insertion into a nare.

8. The harness of claim 1 wherein said sheet members inlcude portions forming a pair of curving tunnels with said other end portions of said tubes respectively received in and surrounded by said tunnels.

9. The harness of claim 1 wherein at least one of said sheet members has a pair of channels in its inner side respectively receiving said other end portions of said tubes to predeterminately locate said other end portions in said bridge.

10. The harness of claim 1 wherein said sheet members comprise a folded single-piece of flexible material having a fold along said bottom side, each of said sheet members has a pair of facing channels extending inwardly respectively from said opposed ends and curving upwardly to said upper side, one of said channels of each of said sheet members receiving and locating one of said other end portions of one of said tubes, the other of said channels of each of said sheet members receiving and locating the said other end portion of the other of said tubes.

11. The harness of claim 1 wherein said harness includes an enlargement extending along said upper side between said other end portions for engagement with the nose of the patient when the harness is in use, and wherein said enlargement includes an integral portion of each of said sheet members and is smoothly rounded.

12. The harness of claim 4 wherein said one side of said bridge is said bottom side thereof.

13. The harness of claim 1 wherein each of said sheet members has at least one curved channel in its inner side for locating at least one tube end portion, and said sheet members are of plastic.

14. The harness of claim 4 wherein said sheet members comprise a folded single-piece of flexible plastic material having a fold along said bottom side.

15. A nasal cannula harness for delivering gas to the nasal passages of a patient comprising a pair of flexible narine tubes each having a proximal end portion adapted for connection with gas supply means and an opposed distal end portion for insertion into a nare of the patient, and a birdge member including a pair of flexible sheet members in facing relation each having a pair of channels in its inner surface, the channels of one of said sheet members being complementary and cooperating respectively with the channels in the inner surface of the other of said sheet members to form a pair of tunnels respectively receiving said distal end portions of said tubes, the inner surfaces of said sheet members being secured together in facing relation at locations on opposed sides on each of said tunnels, said bridge member having opposed ends and upper and lower sides, one of said distal end portions of said tubes and the tunnel receiving the same extending inwardly from one of said opposed ends of said bridge and curving upwardly toward said upper side, and the other of said distal end portions of said tubes and the tunnel receiving the same extending inwardly from the other of said opposed ends of said bridge and curving upwardly toward said upper side, said distal end portions extending outwardly from said upper side of said bridge in spaced relation to each other for insertion into the nares of the patient.

16. The harness of claim 15 wherein said sheet members are of a folded single piece of plastic material having a fold along said lower side of said bridge.

17. The harness of claim 16 wherein each of said distal end portion of said tubes has an annular radial flange adjacent the end thereof insertable into a nare of the patient.

* * * * *